United States Patent [19]
Kido et al.

[11] Patent Number: 6,084,110
[45] Date of Patent: Jul. 4, 2000

[54] STABLE VITAMIN C PREPARATION

[75] Inventors: Takae Kido; Hideto Kodaira; Koji Munechika; Shunichi Abe; Yasuo Ueda, all of Osaka, Japan

[73] Assignee: Welfide Corporation, Osaka, Japan

[21] Appl. No.: 09/043,450

[22] PCT Filed: Sep. 18, 1996

[86] PCT No.: PCT/JP96/02693

§ 371 Date: Oct. 28, 1998

§ 102(e) Date: Oct. 28, 1998

[87] PCT Pub. No.: WO97/10820

PCT Pub. Date: Mar. 27, 1997

[30] Foreign Application Priority Data

Sep. 20, 1995 [JP] Japan ................................. 7-267652

[51] Int. Cl.[7] ................................................. C07D 307/62
[52] U.S. Cl. ........................................................... 549/315
[58] Field of Search ............................. 549/315; 514/474

[56] References Cited

U.S. PATENT DOCUMENTS

| | | | |
|---|---|---|---|
| 5,626,880 | 5/1997 | Inoue et al. | 424/489 |
| 5,674,527 | 10/1997 | Inoue et al. | 424/450 |
| 5,728,681 | 3/1998 | Kido et al. | 514/23 |
| 5,770,233 | 6/1998 | Kido et al. | 424/641 |
| 5,993,863 | 11/1999 | Kikuchi et al. | 424/602 |

FOREIGN PATENT DOCUMENTS

0 312 249 4/1989 European Pat. Off. .
2-212 5/1990 Japan .

*Primary Examiner*—Amelia Owens
*Attorney, Agent, or Firm*—Sughrue, Mion, Zinn, Macpeak & Seas, PLLC

[57] ABSTRACT

This invention relates to a stable vitamin C preparation and a method for stabilizing vitamin C preparation. According to the invention, the vitamin C preparation stable for a long period of time can be obtain, since the preparation contains magnesium ions which have the effect of stabilizing vitamin C.

5 Claims, 1 Drawing Sheet

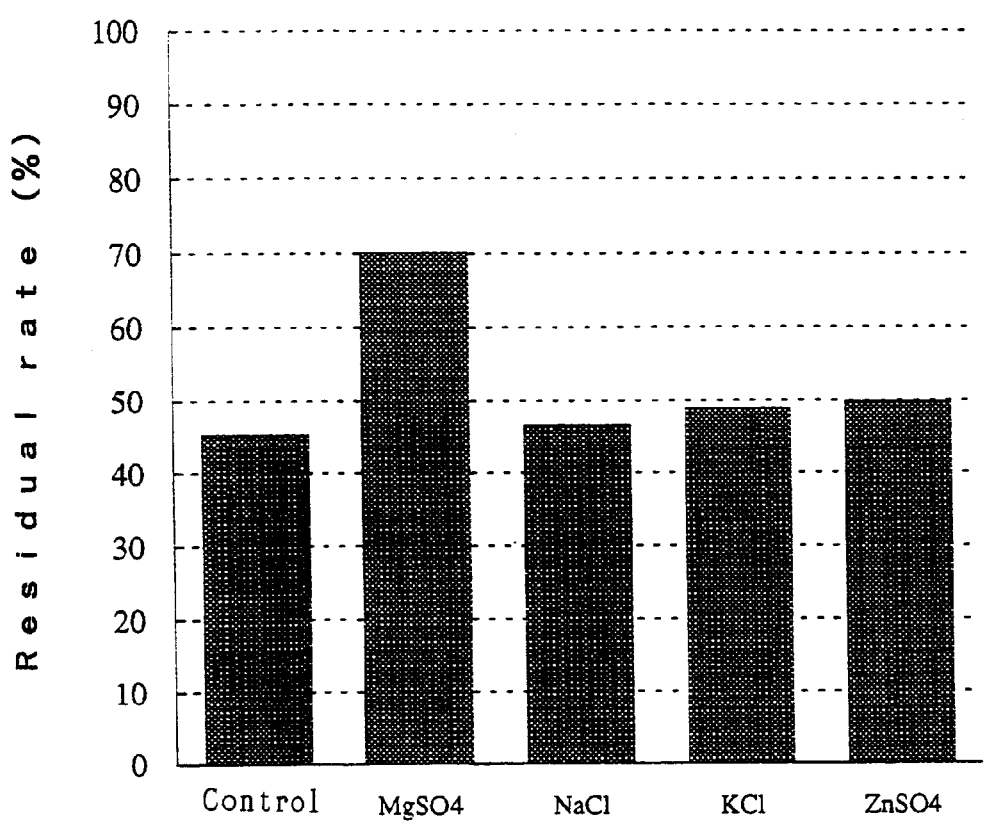

STABLE VITAMIN C PREPARATION

1. Technical Field

The present invention relates to a stable vitamin C preparation which is used in the field of medicine and the like.

2. Prior Art

Recently, in maintenance of patient's life, total parenteral nutrition is employed for nutritional supplement in patients unable to take nutrition orally or enterally, or insufficient in oral intake, or, if possible, in patients extremely poor in the digestion and absorption functions or patients whose underlying diseases may be aggravated by passing of the food through the digestive tract. Such treatment is often accompanied by vitamin preparations containing various vitamins necessary for man.

Many vitamins are, however, unstable per se, and addition of vitamins to an infusion preparation is done immediately before administration to the patients in consideration of the stability of the preparation after addition. Above all, vitamin C (ascorbic acid) is known to be easily decomposed in the presence of oxygen, water, or metal ions such as copper ion or iron ion. From such viewpoint, the stabilization of vitamin C in a vitamin C preparation is an important problem in pharmaceutical technology.

The present inventors attempted various investigations about stabilization of vitamin C in an aqueous solution, and discovered that vitamin C is stabilized in the presence of magnesium ions, which has led to the completion of the invention.

DISCLOSURE OF THE INVENTION

The invention provides a stable vitamin C preparation composed of a vitamin C preparation blended with magnesium ions. In this vitamin C preparation, magnesium ions are preferably contained by 14 parts by weight or more in 100 parts by weight of vitamin C. The vitamin C preparation can be an infusion preparation containing vitamin C. In this case, the vitamin C preparation can be one blended magnesium ions as an electrolyte infusion solution containing magnesium ions, and one blended an electrolyte infusion solution at magnesium ion concentration of 1.5 to 5.0 mEq/liter. Moreover, the vitamin C preparation can be one blended an electrolyte infusion solution containing magnesium ions at magnesium ion concentration of 15 to 35 mEq/liter and further containing at least one component selected from the group consisting of amino acids, sugars and fats.

The invention also relates to a stabilizing method of vitamin C preparation by blending magnesium ions with the vitamin C preparation, and magnesium ions may be blended as an electrolyte infusion solution containing magnesium ions.

In the invention, since magnesium ions having the effect of stabilizing vitamin C are blended, a vitamin C preparation stable for a long period can be obtained.

BRIEF DESCRIPTION OF THE DRAWING

FIG. 1 is a graph showing the residual rate (%) of ascorbic acid after sterilization in Example 1.

BEST MODE FOR CARRYING OUT THE INVENTION

In the invention, the vitamin C preparation is a pharmaceutical preparation containing vitamin C as ingredient, and various forms of preparations are included, and preferably liquid and freeze-dried preparations are exemplified, and more preferably an infusion preparation containing vitamin C is exemplified. The above-mentioned vitamin C includes derivatives of vitamin C, and specific examples include, aside from ascorbic acid, palmitate ascorbate and dipalmitate ascorbate.

Contents of vitamin C to be contained in the vitamin C preparation are not particularly limited, and may be selected appropriately. For example, the daily required amount per person is presented as a recommended value in the literature, such as The Journal of Japanese Society for Parenteral and Enteral Nutrition, Vol. 13, No. 4, p. 317, 1991, and the content may be determined so that the daily required amount may be taken. More specifically, 30 to 2000 mg may be contained.

Further, the vitamin C preparation of the invention is not intended to exclude blending of other components such as vitamins (e.g. vitamin A, vitamin B1, etc.), sugars, amino acids, and electrolytes.

As magnesium ions in the invention, various magnesium salts such as magnesium sulfate, magnesium chloride, magnesium glycerophosphate, magnesium acetate, magnesium lactate and the like may be used and blended.

Contents of magnesium ions to be blended in the vitamin C preparation of the invention are not particularly limited, and may be selected from a wide range appropriately, and magnesium ions are preferably blended by an equimolar amount or more of vitamin C, and specifically magnesium ions are blended by 14 parts by weight or more in 100 parts by weight of vitamin C in the preparation.

The blending method of magnesium ions to the vitamin C preparation is not particularly limited, and an appropriate method may be employed. For example, the blending can be carried out by mixing a proper amount of the magnesium salt with an aqueous solution of vitamin C. Further, a freeze-dried preparation can be prepared by lyophilizing thus obtained solution in a conventional method.

Magnesium ions may be blended alone, but generally since magnesium ions are a part of electrolyte infusion preparation, by blending vitamin C with the electrolyte infusion preparation containing magnesium ions, a stable pre-mixed type electrolyte infusion preparation containing vitamin C may be obtained. In this case, in this infusion preparation, magnesium ions are contained by 14 parts by weight or more in 100 parts by weight of vitamin C, and blended at concentration of 1.5 to 5.0 mEq/liter, which is preferable in order that the intrinsic function of vitamin C can be exhibited, that the stabilizing effect of magnesium ions on vitamin C can be exhibited, and that the magnesium ion concentration in the plasma can be maintained. Moreover, this electrolyte infusion preparation may also contain amino acids commonly used in amino acid infusion solution, and further sugars, fats and the like. When the electrolyte infusion solution contains at least one component selected from the group consisting of amino acids, sugars and fats, magnesium ions are contained by 14 parts by weight or more in 100 parts by weight of vitamin C, and blended at concentration of 15 to 35 mEq/liter, which is preferable in order that the intrinsic function of vitamin C can be exhibited, that the stabilizing effect of magnesium ions on vitamin C can be exhibited, and that the blended amino acids, sugars or fats may be metabolized efficiently.

In the invention, when the vitamin C preparation is a liquid, its liquid properties are not particularly limited, but pH is usually in a range of about 4.0 to 8.0.

According to the invention, as described in Examples mentioned later, the stability of vitamin C is notably improved by blending magnesium ions.

Industrial Applicability

In the vitamin C preparation and stabilizing method of vitamin C preparation of the invention, magnesium ions having the stabilizing action on vitamin C are blended. Therefore, according to the invention, the hitherto unstable vitamin C, in particular, vitamin C in solution can be stabilized, and the vitamin C preparation stable for a long period is obtained.

EXAMPLES

The invention is more specifically described below while referring to Examples, but it must be noted that the invention is not limited by these Examples alone.

Example 1

In 50 mM phosphate buffer (pH 6), magnesium sulfate heptahydrate was dissolved by 2.054 g/liter, and further ascorbic acid (hereinafter referred to as AsA) was dissolved by 0.2 g/liter. The obtained solution was poured into polyethylene bags, replaced with nitrogen, and sterilized under nitrogen pressure for 15 minutes at 115° C. In samples before and after sterilization, AsA was quantitatively determined (the sum of reducing type AsA and oxidizing type AsA, same hereinafter).

As the control, a solution without magnesium sulfate heptahydrate was used, and comparative Examples were prepared by using sodium chloride (1.9485 g/liter), potassium chloride (3.50 g/liter) and zinc sulfate (9.585 mg/liter), instead of magnesium sulfate heptahydrate, and the solutions were similarly treated. AsA in the samples before and after sterilization was determined. Results are shown in Table 1.

The value in Table shows the residual rate (%) of AsA, supposing the amount of AsA added to be 100%. Also supposing the amount of AsA before sterilization to be 100%, the AsA residual rate (%) is shown in FIG. 1. The amount of each component added was set on the basis of the general concentration of addition in the electrolyte infusion preparation.

TABLE 1

|  | $MgSO_4$ | Control | NaCl | KCl | $ZnSO_4$ |
|---|---|---|---|---|---|
| Residual rate before sterilization (%) | 92.63 | 92.98 | 93.02 | 87.62 | 82.82 |
| Residual rate after sterilization (%) | 63.97 | 42.23 | 42.54 | 42.81 | 41.29 |

As shown in Table 1, before sterilization, except for zinc sulfate, the residual rates of AsA in all samples were similar values. After sterilization, however, the AsA residual rates dropped to around 45%, except for the group containing magnesium sulfate. By contrast, in the group containing magnesium sulfate, the AsA residual rate remained around 64%. Also as shown in FIG. 1, the group containing magnesium sulfate presented higher AsA residual rate as compared with the control and comparative Examples containing sodium chloride, potassium chloride and zinc sulfate.

Thus, in the group containing magnesium sulfate, the AsA residual rate remained high even after heat sterilization, and it turned out that magnesium sulfate has a stabilizing effect on AsA. Besides, since the AsA stabilizing effect was not recognized in zinc sulfate, it was clarified that magnesium ion contributes to stabilization of AsA.

Example 2

In the infusion solution containing magnesium ions composed as shown in Table 2, AsA was dissolved by 334 mg/liter, and 50 ml of the solution was poured into each polyethylene bag, and replaced with nitrogen, and subjected to a shower-sterilization for 15 minutes at 115° C. After sterilizing, the sample was put in an oxygen impermeable film container together with disoxidant (trade name: Ageless), which was sealed and stored for a specified period at specified temperature, and then AsA was determined and the residual rate (%) was obtained by supposing the AsA amount before sterilization to be 100% (average of five samples). Results are shown in Tables 3 to 6. The storage temperature and storage period are as follows.

Storage temperature 80° C. (storage period: 0, 12, 24, 48 hours; Table 3)

Storage temperature 60° C. (storage period: 5, 10, 15 days; Table 4)

Storage temperature 40° C. (storage period: 20, 40, 60 days; Table 5)

Storage temperature 25° C. (storage period: 20, 40, 60 days; Table 6)

TABLE 2

| | Component | Concentration (per liter) |
|---|---|---|
| Amino acids | L-Isoleucine | 8.000 g |
| | L-Leucine | 14.000 g |
| | L-Valine | 8.000 g |
| | L-Lysine hydrochloride | 10.000 g |
| | L-Methionine | 4.000 g |
| | L-Phenylamine | 8.000 g |
| | L-Threonine | 6.000 g |
| | L-Tryptophan | 1.200 g |
| | L-Arginine | 10.500 g |
| | L-Histidine | 5.000 g |
| | Glycine | 5.300 g |
| | L-Alanine | 8.500 g |
| | L-Proline | 6.000 g |
| | L-Aspartic acid | 1.500 g |
| | L-Serine | 3.000 g |
| | L-Tyrosine | 0.500 g |
| | L-Glutamic acid | 1.500 g |
| | N-Acetyl-L-cysteine | 1.100 g |
| Organic acids | Calcium gluconate.$1H_2O$ | 6.352 g |
| | Sodium acetate | 6.836 g |
| | Dipotassium glycerophosphate (50%) | 10.688 g |
| | Citric acid | 4.326 g |
| Electrolytes | Sodium chloride | 1.9485 g |
| | Potassium chloride | 3.500 g |
| | Magnesium sulfate.$7H_2O$ | 2.054 g |
| | Zinc sulfate | 9.858 mg |
| | Potassium hydrogensulfite | 0.05 g |

TABLE 3

| | After sterilization | 12 hours | 24 hours | 48 hours |
|---|---|---|---|---|
| Residual rate (%) | 79.70 | 78.58 | 77.59 | 75.21 |

TABLE 4

| | 5 days | 10 days | 15 days |
|---|---|---|---|
| Residual rate (%) | 77.09 | 74.85 | 78.54 |

TABLE 5

|                  | 20 days | 40 days | 60 days |
|------------------|---------|---------|---------|
| Residual rate (%) | 82.70   | 84.16   | 81.90   |

TABLE 6

|                  | 20 days | 40 days | 60 days |
|------------------|---------|---------|---------|
| Residual rate (%) | 82.39   | 83.90   | 84.05   |

As shown in Table 3, by heat sterilization, the residual rate of AsA is lowered to about 20%. However, the AsA residual rate after 48 hours at 80° C. was about 75%, and the drop of residual rate was insignificant.

Also as shown in tables 4 to 6, when stored at 60° C., 40° C. and 25° C., the AsA residual rates were not lowered or lowered only very slightly.

Thus, in the infusion solution containing magnesium ions, it is proved that the stability of vitamin C is enhanced.

What is claimed is:

1. A stable vitamin C infusion preparation composed of a vitamin C preparation blended with an electrolyte infusion solution containing magnesium ions.

2. The stable vitamin C infusion preparation of claim 1, wherein magnesium ions are contained by 14 parts by weight or more in 100 parts by weight of vitamin C.

3. The stable vitamin C infusion preparation of claim 1 or 2, wherein magnesium ions are blended as an electrolyte infusion solution at magnesium ion concentration of 1.5 to 5.0 mEq/liter.

4. The stable vitamin C infusion preparation of claim 3, wherein magnesium ions are blended as an electrolyte infusion solution at magnesium ion concentration of 15 to 35 mEq/liter and further containing at least one component selected from the group consisting of amino acids, sugars and fats.

5. A stabilizing method for a vitamin C infusion preparation comprising blending an electrolyte infusion solution containing magnesium ions with a vitamin C preparation.

* * * * *